(12) United States Patent
Chen et al.

(10) Patent No.: US 6,807,841 B1
(45) Date of Patent: Oct. 26, 2004

(54) DETECTING METHOD OF A DROP TEST AND THE DEVICE THEREOF

(76) Inventors: Shia Chung Chen, 11Fl., No. 14, Lane 236, Sec. 1, Juangjing Rd., Taoyuan City, Taoyuan (TW), 330; Lei Ti Huang, 16Fl., No. 746-1, Shiangshin S. Rd., Nantuen Chiu, Taichung (TW), 408; Chin Chun Chou, No. 31, Lane 39, Sec. 1, Shinglung Rd., Taiping City, Taichung (TW), 412; Wen I Kuo, No. 31, Lane 39, Sec. 1, Shinglung Rd., Taiping City, Taichung (TW), 412; Chia Hung Shih, No. 24, Sec. 1, Linsen Rd., Huwei Jen, Yunlin (TW), 632

( * ) Notice: Subject to any disclaimer, the term of this patent is extended or adjusted under 35 U.S.C. 154(b) by 0 days.

(21) Appl. No.: 10/409,913

(22) Filed: Apr. 8, 2003

(51) Int. Cl.[7] ................................................ G01N 3/52
(52) U.S. Cl. ...................................................... 73/12.06
(58) Field of Search ............................. 73/12.06, 12.01, 73/12.05, 12.09, 12.04, 12.07, 79, 12.13

(56) References Cited

U.S. PATENT DOCUMENTS

| 3,600,932 | A | * | 8/1971 | Hill et al. ................... 73/12.07 |
| 3,871,208 | A | * | 3/1975 | Berg ........................... 73/12.13 |
| 5,390,535 | A | * | 2/1995 | Smock et al. .................... 73/79 |
| 5,540,078 | A | * | 7/1996 | Ambur et al. .............. 73/12.13 |
| 5,567,867 | A | * | 10/1996 | Nazar ......................... 73/12.13 |
| 6,374,661 | B1 | * | 4/2002 | Buratynski et al. ........ 73/12.06 |
| 6,508,103 | B1 | * | 1/2003 | Shim et al. ................ 73/12.06 |

* cited by examiner

Primary Examiner—Edward Lefkowitz
Assistant Examiner—Octavia Davis
(74) Attorney, Agent, or Firm—Charles E. Baxley (57) ABSTRACT

A detecting method can perform the drop test according to the exact grounding condition, thereby detecting the actual grounding data. In addition, the shock accelerometer on the tested point of the test object can obtain an experimented G value which is compared with the simulated G value that is obtained by inputting the grounding angles (the grounding angles are calculated according to the grounding pictures) into the simulation program. In addition, the drop test device can reduce interruption, thereby enhancing the whole detecting accuracy.

10 Claims, 7 Drawing Sheets

DETECTING METHOD OF A DROP TEST AND THE DEVICE THEREOF

BACKGROUND OF THE INVENTION

1. Field of the Invention

The present invention relates to a detecting method of a drop test and the device thereof, and more particularly to a detecting method that can perform the drop test according to the exact grounding condition, thereby detecting the actual grounding data.

2. Description of the Related Art

The closest prior art of which the applicant is aware is disclosed in PCT Patent No. WO-00/77487-A1, entitled "IMPACT DROP TESTER FOR PORTABLE CONSUMER PRODUCTS".

The above-mentioned drop tester includes an upper slide seat having an electromagnet, and a lower slide seat attached on the electromagnet. In operation, the motor drives the cable to lift to a determined height. When the electric power of the electromagnet is shut, the lower slide seat falls down, so that the test object hits the piezoelectric sensing platform, so as to test the structural strength of the test object. However, the camera is mounted on the piezoelectric sensing platform. Thus, when the test object drops and hits the piezoelectric sensing platform, the piezoelectric sensing platform easily produces vibration, thereby affecting the accuracy of the camera which easily produces erroneous data, thereby decreasing the accuracy of the drop test.

SUMMARY OF THE INVENTION

The primary objective of the present invention is to provide a detecting method of a drop test, wherein the detecting method can perform the drop test according to the exact grounding condition, thereby detecting the actual grounding data.

Another objective of the present invention is to provide a drop test device that can reduce interruption, thereby enhancing the whole detecting accuracy.

Further benefits and advantages of the present invention will become apparent after a careful reading of the detailed description with appropriate reference to the accompanying drawings.

DETAILED DESCRIPTION OF THE INVENTION

Referring to the drawings and initially to FIGS. 1–5, a drop test device in accordance with the preferred embodiment of the present invention comprises a main frame 10 having a bottom board 11, a slide seat 30 mounted on an upper portion of the main frame 10, and a clamping device 40 mounted on the slide seat 30 for clamping a test object 70. Thus, when the slide seat 30 drops relative to the main frame 10 in a free falling manner and the test object 70 is released and hit, the shock tolerance of the test object 70 can be measured and calculated. The above-mentioned structure and principle of operation are conventional, and will not be further described in detail.

The main frame 10 includes a bottom board 11, a plurality of rollers 12 mounted on the bottom face of the bottom board 11 for movement of the drop test device, a plurality of height adjustable support foots 13 mounted on the bottom face of the bottom board 11 for maintaining stability and level of the drop test device, two parallel upward extending slide rods 15 mounted on the rear side of the bottom board 11 for sliding of the slide seat 30, two buffer elastic members 16 each mounted on the lower portion of the respective slide rod 15 to provide a buffer effect to the slide seat 30, a top plate 17 straddled on the top of the two slide rods 15, an upward extending upright column 18 mounted on the rear side of the bottom board 11 and located adjacent to the two slide rods 15, a positioning unit 20 mounted on the upper portion of the upright column 18 and having a positioning pin 21 for positioning the slide seat 30 on the top of the two slide rods 15, a plurality of, preferably two, proximity sensors 25 mounted on the upright column 18 to decide the height where the clamping device 40 releases the test object 70, and an infrared sensor 26 mounted between the two proximity sensors 25 to verify operation of the slide seat 30 and start the timing action.

The slide seat 30 includes a back plate 31 straddled on the two slide rods 15. The back plate 31 is provided with two pairs of spaced slide jackets 32 each slidably mounted on the respective slide rod 15 to enhance the sliding effect of the slide seat 30. The slide jacket 32 located at the lower position has a back face provided with a photosensitive plate 320 aligning with the infrared sensor 26 to enhance the sensing effect of the infrared sensor 26. The back plate 31 is provided with a counterweight bracket 33 and a pivot base 34 located under the counterweight bracket 33. The pivot base 34 has two L-shaped pivot plates 35 each pivotally mounted on the pivot base 34 by a pivot shaft (not labeled) and each having a distal end provided with a clamping plate 36 for clamping the test object 70. The top plate 17 straddled on the two slide rods 15 is provided with a first roller 370 and a second roller 375, and a cable 38 having a first end reeved on the first roller 370 and second roller 375 and secured on the back plate 31 of the slide seat 30 and a second end provided with a locking bolt 39 for hanging a counterweight 391 for calculating the counterweight of the slide seat 30.

The clamping device 40 is mounted on the back face of the slide seat 30 and includes a flat plate 41 mounted on the back plate 31 of the slide seat 30, and an electromagnetic valve 42 mounted on the flat plate 41 and having an operation rod (not labeled) connected to a first end of a T-shaped brake plate 45. Each of the two pivot plates 35 of the pivot base 34 is pivotally mounted on the second end of the brake plate 45. Thus, when the electromagnetic valve 42 controls the brake plate 45 to move forward and backward, the two pivot plates 35 of the pivot base 34 are pivoted to drive the clamping plates 36 to release the test object 70 as shown in FIG. 4 or to clamp the test object 70 as shown in FIG. 3.

The drop test device further comprises a piezoelectric sensing platform 50 mounted on the bottom board 11 of the main frame 10. The piezoelectric sensing platform 50 has a bottom face provided with a plurality of support foots 51 rested on the ground, so that the main frame 10 will not interfere with the piezoelectric sensing platform 50. The bottom face of the piezoelectric sensing platform 50 is also provided with a plurality of rollers 52. The drop test device further comprises an L-shaped slide track 60 mounted around the main frame 10 and having a bottom face provided with a plurality of support foots 61 rested on the ground, so that the slide track 60 will not interfere with the main frame 10 or the piezoelectric sensing platform 50. The slide track 60 is provided with at least two CCD cameras 65 that can produce pictures of two angles when the test object 70 hits the piezoelectric sensing platform 50 to function as the basis of calculation. The piezoelectric sensing platform 50 is provided with a reflective mirror 66 having an inclined angle of 45 degrees relative to the two CCD cameras 65. Thus, when the two CCD cameras 65 are taking the same photographs, the two CCD cameras 65 can simultaneously obtain the mode of another angle of the test object 70 hitting the piezoelectric sensing platform 50 presented by the reflective mirror 66, thereby forming pictures of two angles to function as the basis of calculation.

Figure 7:
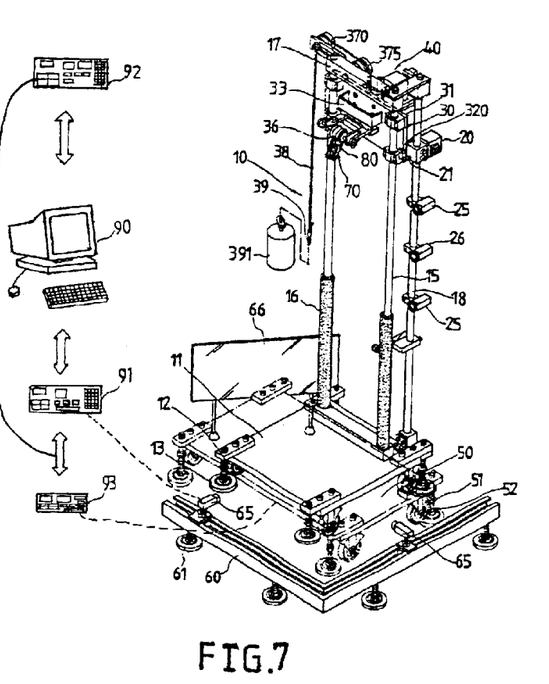
FIG. 7 is a practice view of the drop test device as shown in FIG. 1.
Figure 7A:
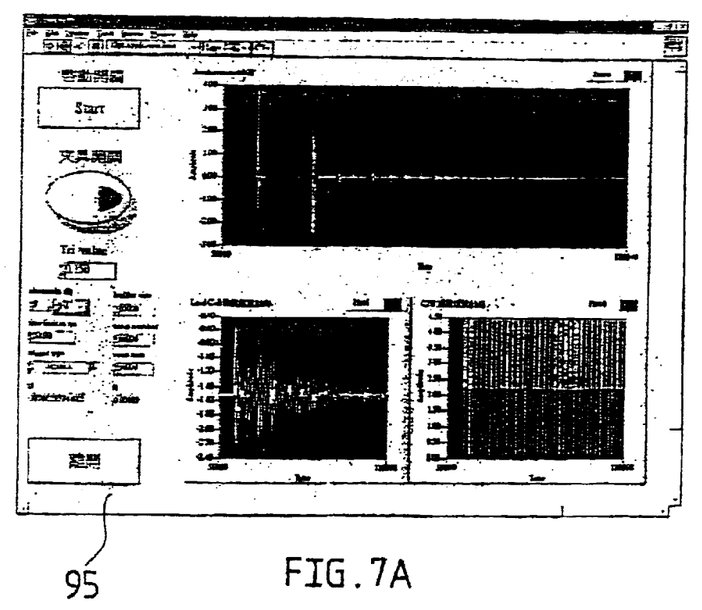
FIG. 7A is a diagram of the monitoring program of the drop test in accordance with the preferred embodiment of the present invention.

Referring to FIGS. 7 and 7A, a shock accelerometer 80 is attached on the tested point of the test object 70 and is connected to the accelerometer signal capture card 92 of the computer 90, the two CCD cameras 65 are connected to the image capture card 91 of the computer 90, and the piezoelectric sensing platform 50 is connected to the PCB 93 of the computer 90 and is controlled by the monitoring program 95, thereby forming the drop test device that can perform the drop test without being interrupted.

Figure 1:
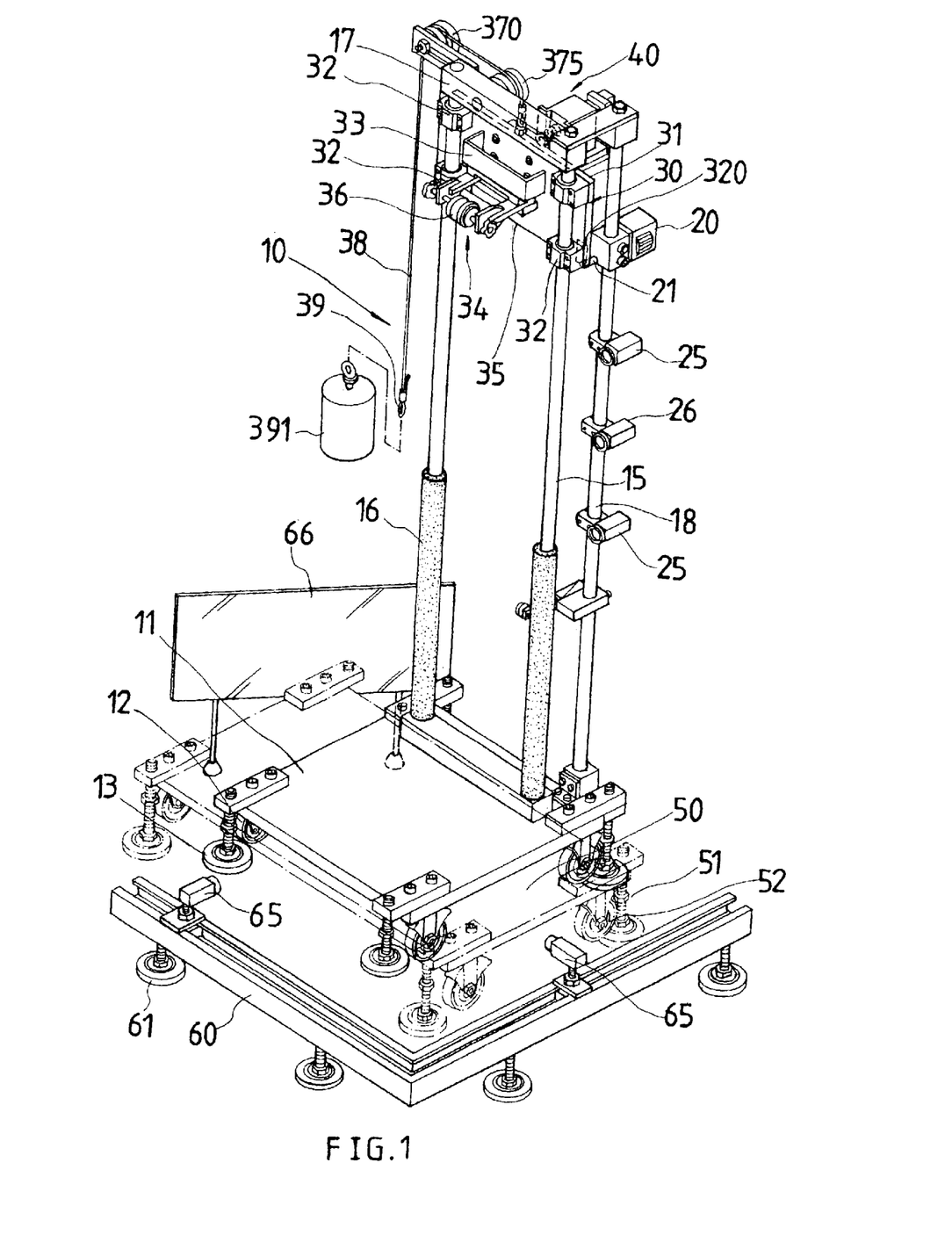
FIG. 1 is a perspective view of a drop test device in accordance with the preferred embodiment of the present invention.
Figure 2:
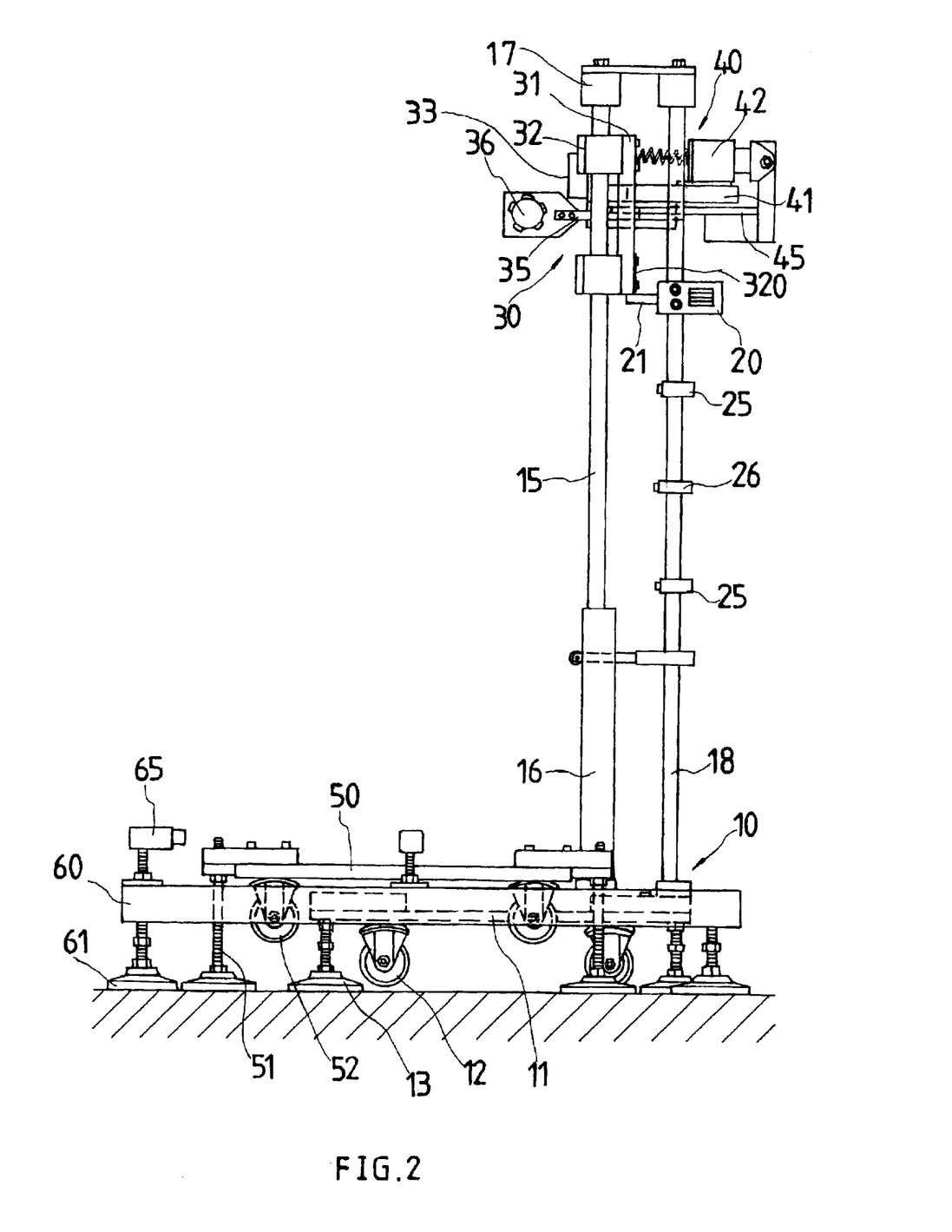
FIG. 2 is a side plan view of the drop test device as shown in FIG. 1.
Figure 3:
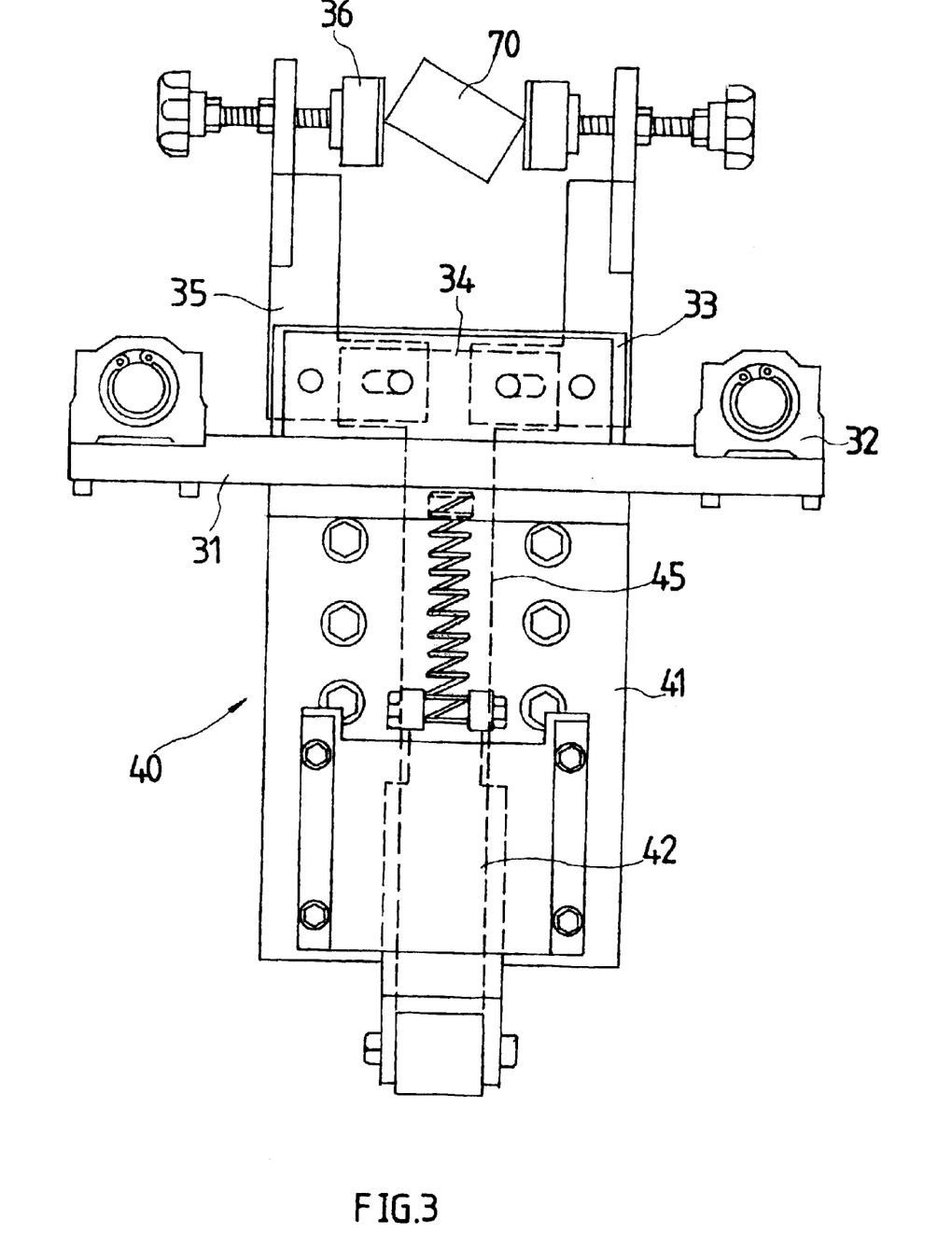
FIG. 3 is a top plan view of the drop test device as shown in FIG. 1.
Figure 4:
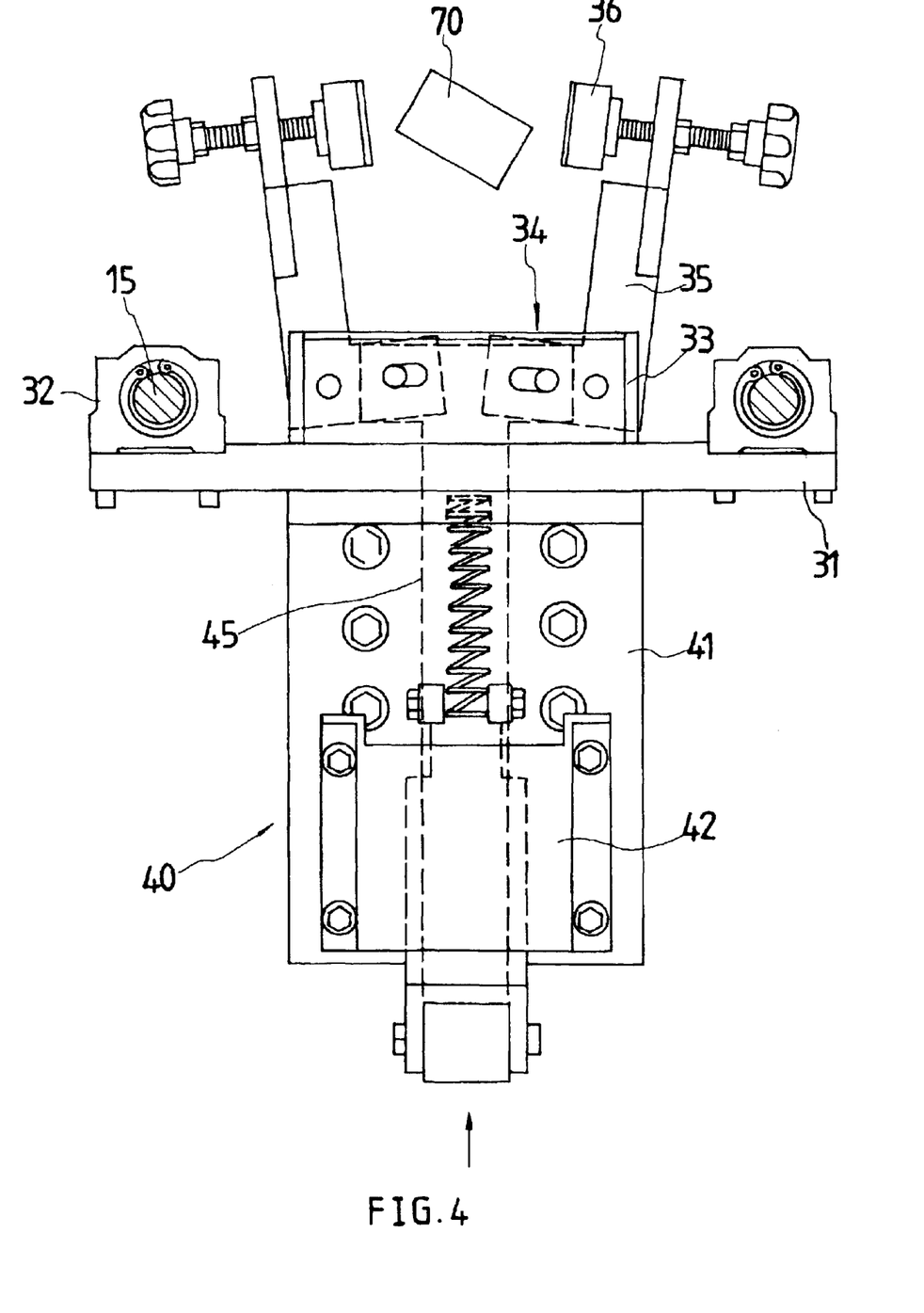
FIG. 4 is a schematic operational view of the drop test device as shown in FIG. 3.
Figure 5:
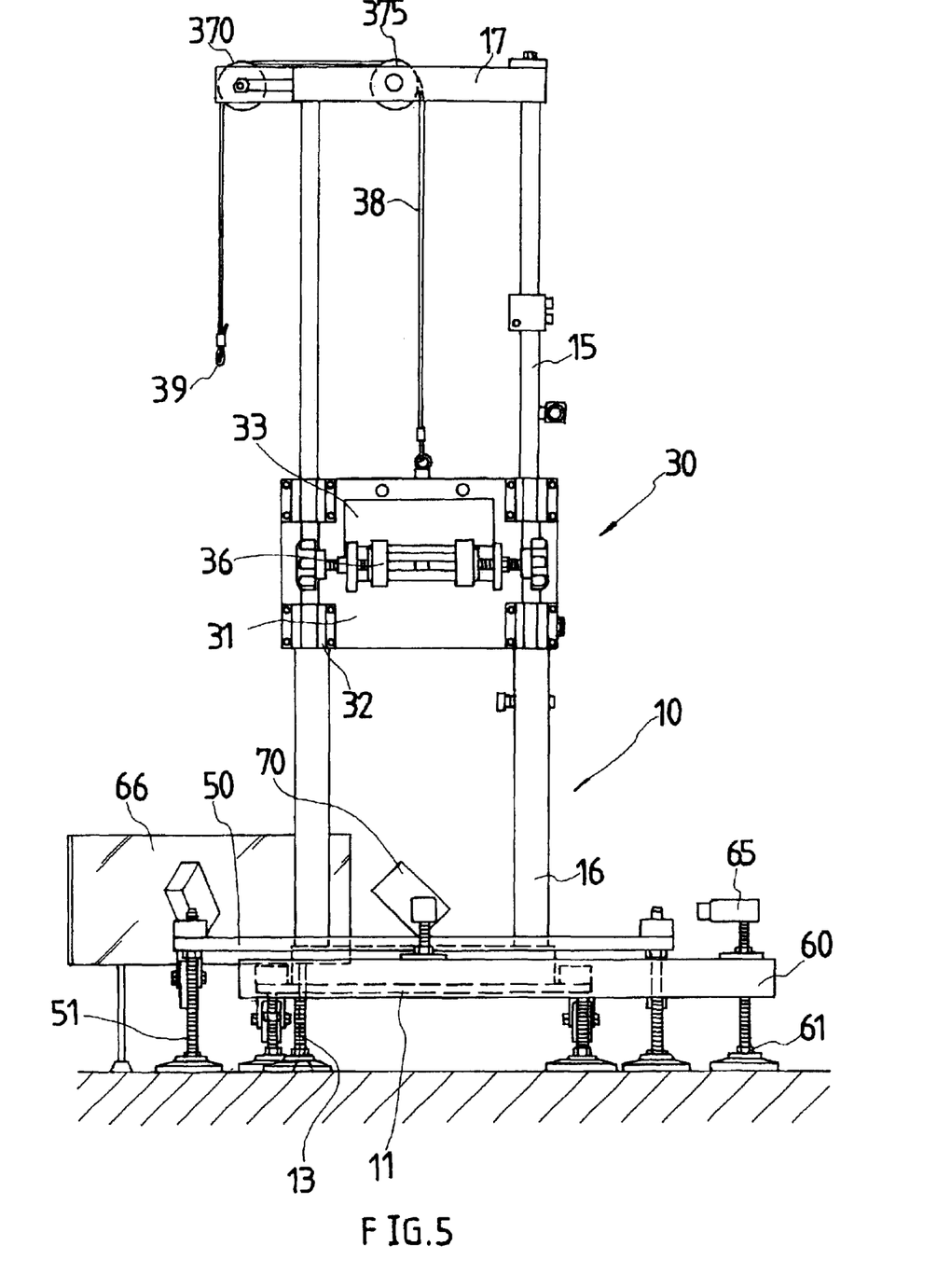
FIG. 5 is a front plan view of the drop test device as shown in FIG. 1.

In practice, referring to FIGS. 1–5, the counterweight 391 is hung on the locking bolt 39 of the cable 38 to measure the weight of the counterweight that is placed on the counterweight bracket 33 of the slide seat 30. Then, the counterweight 391 is removed from the locking bolt 39 of the cable 38. Then, the positioning pin 21 of the positioning unit 20 mounted on the upright column 18 is used for positioning the slide seat 30 at a fixed height on the two slide rods 15. Then, the electromagnetic valve 42 of the clamping device 40 is operated to open the clamping plates 36. Then, after the test object 70 is placed between the clamping plates 36, the electromagnetic valve 42 of the clamping device 40 is operated to drive the clamping plates 36 to clamp the test object 70 as shown in FIG. 3. Then, the height of the two proximity sensors 25 is adjusted to decide the determined height where the clamping device 40 releases the test object 70. Then, the user only needs to start the positioning unit 20 to release the slide seat 30, so that the slide seat 30 is accelerated to fall down due to effect of the counterweight. After the infrared sensor 26 detects falling of the slide seat 30, the infrared sensor 26 starts the timing action. When the proximity sensor 25 detects that the slide seat 30 is falling to the determined height, the proximity sensor 25 sends a signal to the electromagnetic valve 42 of the clamping device 40 to drive the clamping plates 36 to release the test object 70, so that the test object 70 hits the piezoelectric sensing platform 50. At the same time, the two CCD cameras 65 are started to record the complete falling condition and the hit points, so as to measure the practical drop data actually, thereby enhancing the whole testing quality, and thereby preventing the unnecessary interruption.

Figure 6:
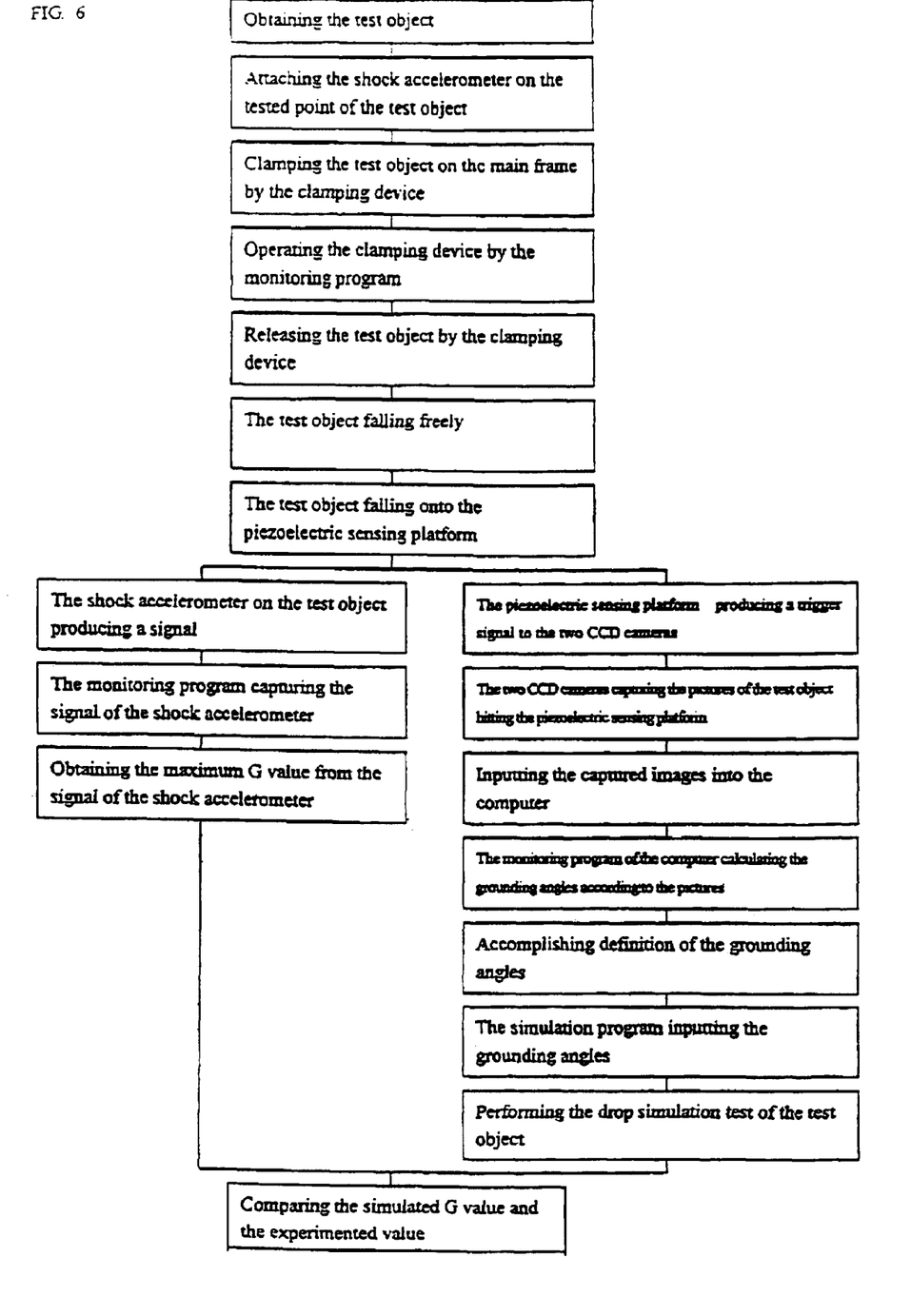
FIG. 6 is a flow chart of a detecting method of a drop test in accordance with the preferred embodiment of the present invention.

Referring to FIGS. 6, 7 and 7A, the detecting method of the drop test includes the following steps:

1. performing an empty load test;
2. calibrating the load of the counterweight bracket 33 according to the results of the empty load test to adjust the velocity of the free falling body;
3. increasing the load of the counterweight bracket 33 according to an external force to be tested to simulate the condition when the test object 70 is hit by the external force;
4. obtaining the test object 70;
5. attaching the shock accelerometer 80 on the tested point of the test object 70;
6. clamping the test object 70 on the main frame 10 by the clamping device 40;
7. operating the clamping device 40 by the monitoring program 95;
8. releasing the test object 70 by the clamping device 40;
9. the test object 70 falling freely;
10. the test object 70 falling onto the piezoelectric sensing platform 50 (producing the action of steps ~A" and ~I" simultaneously);
   A. the shock accelerometer 80 on the test object 70 producing a signal;
   B. the monitoring program 95 capturing the signal of the shock accelerometer 80;
   C. obtaining the maximum G value from the signal of the shock accelerometer 80 (performing the action of step 11);
   I. the piezoelectric sensing platform 50 producing a trigger signal to the two CCD cameras 65;
   II. the two CCD cameras 65 capturing the pictures of the test object 70 hitting the piezoelectric sensing platform 50;
   III. inputting the captured images into the computer 90;
   IV. the monitoring program 95 of the computer 90 calculating the grounding angles according to the pictures;
   V. accomplishing definition of the grounding angles;
   VI. the simulation program inputting the grounding angles;
   VII. performing the drop simulation test of the test object 70 (performing the action of step 11); and
11. comparing the simulated G value and the experimented value.

The procedures of action are described as follows.

First of all, the test object 70 is hung above the piezoelectric sensing platform 50 and is clamped by the clamping device 40. Then, the shock accelerometer 80 is attached on the tested point of the test object 70. Then, the monitoring program 95 sends a start command (see FIGS. 7 and 7A) to operate the electromagnetic valve 42 of the clamping device 40 to drive the clamping plates 36 to release the test object 70. Then, the data of the sensors are recorded during two seconds, wherein the sensors includes the shock accelerometer 80 and the trigger signal of the piezoelectric sensing platform 50. When the test object 70 hits the piezoelectric sensing unit (not shown) mounted on the piezoelectric sensing platform 50, the piezoelectric sensing platform 50 triggers the trigger circuit (including the piezoelectric sensing unit trigger line and the shock accelerometer trigger circuit) to start the two CCD cameras 65 to successively capture the pictures of the test object 70 hitting the piezoelectric sensing platform 50. The sensors detects the above procedures and send the data to the data capture card, and the monitoring program 95 reads and records the data. In addition, the two CCD cameras 65 capture the image pictures which are recorded by the program during two seconds, and sixty frames of the image pictures are taken, thereby accomplishing the whole monitoring action. Thus, the drop test of the test object 70 is performed in a free falling or accelerated manner with the minimum interruption of the external force. In addition, the shock accelerometer 80 on the tested point of the test object 70 can obtain the maximum G value (experimented value) which is compared with the simulated G value that is obtained by inputting the grounding angles (the grounding angles are calculated according to the grounding pictures) into the simulation program. If the maximum G value approximates the simulated G value, the drop hitting G value and the position are correct. If the error exists, the user has to consider the related interruption factors of the testing environment, so as to obtain the optimum drop hitting G value and position.

Attachment 1 is the formula of calculation of the drop test, and attachment 2 is the images of the test object 70 captured by the CCD cameras 65. Thus, the grounding angle of the test object 70 can be calculated according to attachment 1 and attachment 2.

While the preferred embodiment(s) of the present invention has been shown and described, it will be apparent to those skilled in the art that various modifications may be made in the embodiment(s) without departing from the spirit of the present invention. Such modifications are all within the scope of the present invention.

What is claimed is:

1. A detecting method of a drop test, using a drop test platform, a PCB, an image capture card, a shock accelerometer, a clamping device, and a plurality of CCD cameras, comprising the steps of:
 (1) performing an empty load test;
 (2) calibrating the load of the counterweight bracket according to the results of the empty load test to adjust the velocity of the free falling body;
 (3) increasing the load of the counterweight bracket according to an external force to be tested to simulate the condition when the test object is hit by the external force;
 (4) obtaining the test object;
 (5) attaching the shock accelerometer on the tested point of the test object;
 (6) clamping the test object on the main frame by the clamping device;
 (7) operating the clamping device by the monitoring program;
 (8) releasing the test object by the clamping device;
 (9) the test object falling freely;
 (10) the test object falling onto the piezoelectric sensing platform (producing the action of steps A and I simultaneously);
 A. the shock accelerometer on the test object producing a signal;
 B. the monitoring program capturing the signal of the shock accelerometer;
 C. obtaining a maximum G value from the signal of the shock accelerometer (performing the action of step 11);
 I. the piezoelectric sensing platform producing a trigger signal to the CCD cameras;
 II. the CCD cameras capturing the pictures of the test object hitting the piezoelectric sensing platform;
 III. inputting the captured images into the computer;
 IV. the monitoring program of the computer calculating the grounding angles according to the pictures;
 V. accomplishing definition of the grounding angles;
 VI. a simulation program inputting the grounding angles;
 VII. performing the drop simulation test of the test object (performing the action of step 11); and
 (11) comparing a simulated G value and an experimented value.

2. A drop test device, comprising a main frame having a bottom board, a slide seat mounted on an upper portion of the main frame, and a clamping device mounted on the slide seat for clamping a test object, wherein:
 the main frame includes two parallel upward extending slide rods mounted on the rear side of the bottom board for sliding of the slide seat, two buffer elastic members each mounted on the lower portion of the respective slide rod, a top plate straddled on the top of the two slide rods, an upward extending upright column mounted on the rear side of the bottom board and located adjacent to the two slide rods, a positioning unit mounted on the upper portion of the upright column for positioning the slide seat, a proximity sensor mounted on the upright column to detect drop of the slide seat;
 the slide seat includes a back plate straddled on the two slide rods, the back plate is provided with two pairs of spaced slide jackets each slidably mounted on the respective slide rod, the back plate is provided with a counterweight bracket, the top plate is provided with a first roller and a second roller, and a cable having a first end reeved on the first roller and second roller and secured on the back plate of the slide seat and a second end provided with a locking bolt for hanging a counterweight;
 the drop test device further comprises a piezoelectric sensing platform mounted on the bottom board of the main frame, the piezoelectric sensing platform is provided with at least two CCD cameras;
 a shock accelerometer is attached on the tested point of the test object and is connected to the accelerometer signal capture card of a computer, the CCD cameras are connected to the image capture card of the computer, and the piezoelectric sensing platform is connected to a PCB of the computer and is controlled by the monitoring program, thereby forming the drop test device.

3. The drop test device in accordance with claim 2, wherein the main frame includes a plurality of rollers mounted on the bottom face of the bottom board for movement of the drop test device.

4. The drop test device in accordance with claim 2, wherein the main frame includes a plurality of height adjustable support foots mounted on the bottom face of the bottom board for maintaining stability and level of the drop test device.

5. The drop test device in accordance with claim 2, further comprising a clamping device including a flat plate mounted on the back plate of the slide seat, and an electromagnetic valve mounted on the flat plate and having an operation rod connected to a first end of a T-shaped brake plate, wherein the back plate is provided with a pivot base located under the counterweight bracket, the pivot base has two L-shaped pivot plates each pivotally mounted on the pivot base by a pivot shaft and each having a distal end provided with a clamping plate for clamping the test object.

6. The drop test device in accordance with claim 2, wherein the piezoelectric sensing platform has a bottom face provided with a plurality of rollers.

7. The drop test device in accordance with claim 2, wherein the piezoelectric sensing platform has a bottom face provided with a plurality of support foots rested on the ground, so that the main frame will not interfere with the piezoelectric sensing platform.

8. The drop test device in accordance with claim 2, further comprising an L-shaped slide track mounted around the main frame and having a bottom face provided with a plurality of support foots rested on the ground, so that the slide track will not interfere with the main frame and the piezoelectric sensing platform, wherein the at least two CCD cameras are mounted on the slide track.

9. The drop test device in accordance with claim 2, further comprising an infrared sensor mounted between the proximity sensors to verify operation of the slide seat and start the timing action, wherein the slide jacket has a back face provided with a photosensitive plate aligning with the infrared sensor to enhance the sensing effect of the infrared sensor.

10. The drop test device in accordance with claim 2, wherein the piezoelectric sensing platform is provided with a reflective mirror having an inclined angle of 45 degrees relative to the CCD cameras, so that when the CCD cameras are taking the same photographs, the CCD cameras can simultaneously obtain the mode of another angle of the test object hitting the piezoelectric sensing platform presented by the reflective mirror, thereby forming pictures of two angles to function as the basis of calculation.

* * * * *